United States Patent [19]

Burkholder

[11] 4,132,695

[45] Jan. 2, 1979

[54] ABSORBENT ARTICLES AND METHODS FOR THEIR PREPARATION

[75] Inventor: Nelson D. Burkholder, Castro Valley, Calif.

[73] Assignee: The Dow Chemical Company, Midland, Mich.

[21] Appl. No.: 792,163

[22] Filed: Apr. 29, 1977

Related U.S. Application Data

[63] Continuation-in-part of Ser. No. 565,880, Apr. 7, 1975, abandoned.

[51] Int. Cl.$^2$ ............................................. C08L 33/02
[52] U.S. Cl. .................. 260/29.6 NR; 260/29.2 EP; 260/33.4 EP; 260/29.6 TA
[58] Field of Search ................ 260/29.6 NR, 29.2 EP, 260/33.4 EP, 29.6 TA

[56] References Cited

U.S. PATENT DOCUMENTS

| | | | |
|---|---|---|---|
| 3,224,986 | 12/1965 | Butler et al. | 260/9 R |
| 3,660,338 | 5/1972 | Economou | 260/29.6 NR |
| 3,669,103 | 6/1972 | Harper et al. | 128/156 |
| 3,670,731 | 6/1972 | Harmon | 260/29.6 R |
| 3,926,891 | 12/1975 | Gross et al. | 260/29.6 TA |

*Primary Examiner*—M. J. Welsh
*Attorney, Agent, or Firm*—B. G. Colley

[57] ABSTRACT

Water absorbent articles, made from solutions of carboxylic polyelectrolytes, together with methods for their preparation, and a composition useful to make said articles are disclosed. The articles are cured and/or crosslinked with polyamido-polyamine epichlorohydrin adducts by heating and/or removing substantially all of the solvent from the precursor composition.

The absorbent articles are useful as surgical sponges, diapers, tampons, meat trays, bath mats and the like.

8 Claims, No Drawings

ABSORBENT ARTICLES AND METHODS FOR THEIR PREPARATION

CROSS-REFERENCE TO RELATED APPLICATIONS

This application is a continuation-in-part of Ser. No. 565,880, filed Apr. 7, 1975 now abandoned.

BACKGROUND OF THE INVENTION

This invention relates to water absorbent articles made from crosslinked polyelectrolytes, methods for their preparation, and to a composition containing polyelectrolytes and polyamido-polyamine/epichlorohydrin adducts which is useful to make absorbent articles.

It is known from U.S. Pat. Nos. 3,669,103 and 3,670,731 the cross-linked polymeric sorbents can be sandwiched between flexible supports to achieve disposable diapers or dressings.

It is further known from 2,988,539; 3,393,168; 3,514,419 and 3,357,067 that water absorbent crosslinked carboxylic copolymers can be prepared. However, these prior art copolymers are all crosslinked during copolymerization or crosslinked after polymerization with subsequent neutralization of the carboxylic acid groups to form water absorbent polyelectrolytes and hence these prior art polyelectrolytes cannot be crosslinked in situ as a coating on a substrate or as a flexible film thereof.

The polyamido-polyamine epichlorohydrin adducts used herein have been used to cure water soluble polymers to water insoluble films as is shown by U.S. Pat. No. 3,224,986 to Butler, et al. However, this patent does not indicate how to make water absorbent products.

The foregoing adducts are believed to be water soluble resins having a plurality of 3-hydroxy azetidinium, epoxy propyl, and chlorohydrin groups as is shown by Carr, et al., J. Applied Polymer Science 17:721–735 (1973).

SUMMARY OF THE INVENTION

The patent to J. R. Gross, 3,980,663, discloses methods of curing polyelectrolytes to water absorbent articles wherein the curing or crosslinking agent is a polyhaloalkanol, a sulfonium zwitterion, a haloepoxyalkane or a polyglycidyl ether.

It now has been discovered that faster cures, at lower temperatures, can be obtained by using polyamido-polyamine epichlorohydrin adducts.

The present invention comprises a composition which is useful to form water absorbent articles of a carboxylic type synthetic polyelectrolyte which consists of lower alcohols, water, or mixtures thereof, about 5 to about 60 percent, preferably about 15 to about 40 percent by weight based on the solvent of a carboxylic polyelectrolyte, and an amount of a water soluble polyamido-polyamine/epichlorohydrin adduct sufficient to cure the polyelectrolyte into a water absorbent article.

The invention further comprises methods of making discrete films, absorbent articles, particulates, fibers, and the products of these processes wherein the above composition on various substrates, is dried to crosslink the polyelectrolyte. The use of elevated temperatures is advantageous to accelerate the crosslinking and drying of the polyelectrolyte. However, if desired, the use of heat can be eliminated.

In order to obtain very high production rates of absorbent articles, it may be desirable to replace part of nearly all of the water in the polyelectrolyte solution with a lower alcohol such as methanol or ethanol. This substitution results in lower solution viscosities at a given percent solids and promotes rapid drying.

The final products of the present invention are thus water absorbent and are useful where ever aqueous solutions need to be absorbed. Examples of the diverse utilities are surgical sponges, catamenial tampons, diapers, meat trays, paper towels, disposable door mats, disposable bath mats and disposable litter mats for household pets.

DETAILED DESCRIPTION

Examples of carboxylic synthetic polyelectrolytes useful in this invention are the ammonium or alkali metal salts of homopolymers of acrylic or methacrylic acid and copolymers of acrylic acid, methacrylic acid, maleic acid, fumaric acid or maleic anhydride with one or more ethylenically unsaturated comonomers such as vinyl acetate, styrene, styrene sulfonic acid, acrylamide and the like. The only limitation being that any copolymer, to be useful in preparing highly absorbent polymers according to this invention, must be essentially water soluble in the salt form. The alternating copolymers of maleic anhydride and the maleic and fumaric acids and esters are useful when rendered water soluble by an appropriate base. One skilled in the art of radical addition copolymerization could prepare any number of suitable heteropolymers containing sufficient carboxylate functionality to render them water soluble and thus be useful in this invention.

A list of applicable carboxylic polymers which could be prepared from readily available monomers and converted into their salt form is as follows:
- acrylic acid — acrylate copolymers,
- acrylic acid — acrylamide copolymers,
- acrylic acid — olefin copolymers, polyacrylic acid,
- acrylic acid — vinyl aromatic copolymers,
- acrylic acid — styrene sulfonic acid copolymers,
- acrylic acid — vinyl ether copolymers,
- acrylic acid — vinyl acetate copolymers,
- acrylic acid — vinyl alcohol copolymers,
- copolymers of methacrylic acid with all the above comonomers,
- copolymers of maleic acid, fumaric acid and their esters with all the above comonomers,
- copolymers of maleic anhydride with all the above comonomers.

If desired, the foregoing polyelectrolytes can also be sulfonated by treatment with $SO_3$, chlorosulfonic acid or fuming sulfuric acid in an inert organic solvent.

Illustrative examples of the crosslinking agents useful in this invention are set forth in U.S. Pat. Nos. 2,926,154; 3,224,986; and 3,332,901. The disclosures of these references are incorporated herein by reference.

In the preferred method of making water swellable films by the present invention, the above composition of the polyelectrolytes is spread on a flat plate or roller of metal, plastic or other impervious substrate and dried to crosslink the polyelectrolyte and drive off the excess water and/or alcohol. The flm is then peeled off the plate or roller by a scraper to recover the intact film for subsequent storage or use.

It is sometimes desirable to add a small amount of surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and the ethylene oxide derivatives of alkylated phenols and the like.

Similarly, when an absorbent article is prepared, the article which is to be the substrate is coated with the composition of the polyelectrolyte and then the coating is crosslinked. It is to be understood that for the purposes of this invention the coating step implies a complete coating or a discontinuous coating, thus when a fibrous substrate such as cellulose batting, paper, woven or non-woven cloth, polyurethane foam and the like are used as the substrate, the composition can be applied in a discontinuous manner, i.e., in a pattern of large dots, squares, or grid lines to retain the inherent flexibility of the fiberous substrate and at the same time vastly improve its water absorbency. Wood pulp can be coated by slurrying it in the polyelectrolyte composition followed by a fluffing operation.

If desired, the water absorbent film prepared as above can be used per se as the inner absorbent layer in baby diapers. It is sometimes advantageous that the film by disintegrated into flakes, strips or powders. This is accomplished by crushing or comminuting the film in a hammer mill, blenders, or the like. If long flat strips are desired, the film can be sliced widthwise with appropriate slicers.

In some instances, water absorbent fibers are desired. These can be prepared by extruding the above composition of the polyelectrolytes into a bath comprising lower alkyl ketones such as acetone, methyl ethyl ketone, diethyl ketone and the like. Alcoholic compositions may be extruded into a non-aqueous coagulant such as chlorinated hydrocarbons, i.e., methylene chloride, perchloroethylene and the like. The soft extruded fibers are then removed from the bath by any convenient means such as a three or five roll cluster and carried through a heated chamber at a temperature greater than about 30° C. and preferably in the range from about 70° to about 150° C. to dry and to crosslink the polyelectrolyte fibers.

The absorbency of the crosslinked polyelectrolytes (grams solution gelled per gram of polyelectrolyte) is determined in the following manner using synthetic urine (0.27 N sodium chloride solution).

A 0.5 gram sample of a crosslinked polyelectrolyte is weighed into a 250 ml. beaker, a 0.27 N sodium chloride solution (150 ml.) is poured into the beaker and allowed to soak for 15 minutes at room temperature, with occasional stirring. The polyelectrolyte is then collected by filtration and the gel capacity or absorbency is reported as grams of solution gelled per gram of polymer salt (g/g).

The gel capacity or absorbency can also be expressed as precent saline solution absorbed. Thus, if the absorbency of the gel is 20 grams of solution per gram of polymer the percent solution absorbed is 1900%. This is calculated as follows:

$$\frac{(gms\ after - gms\ before) \times 100}{gms\ before}\ or$$

$$\frac{(20-1) \times 100}{1} = 1900\%$$

It is to be emphasized that the utility of this invention is not restricted to the absorption of saline solutions but can be applied to the absorption of relatively pure water as when the ultimate use is paper towels, door mats, bath mats, etc. In these cases, the above percentage of absorption and gel capacity is increased by a factor of 5 or 6.

For the purposes of this invention, a moisture or water absorbent polyelectrolyte is defined as one which absorbs greater than about 20 times its weight of synthetic or natural urine. Preferably, the absorbency should be in the range from about 30–60 grams of urine per gram of resin or polyelectrolyte. As can be seen from Table III hereinafter, the level of crosslinking agent (Kymene 557) used is a variable factor which is dependent upon the particular polyelectrolyte used and the molecular weight of the polyelectrolyte. In general, the amount used varies from about 0.5 to 5.0 percent based on the weight of the polyelectrolyte. However, this range is varied for each polyelectrolyte in order to adjust the absorbency of the final crosslinked gel so that it is at least 20 preferably in the range from about 30 to about 60 grams of urine per gram of resin.

EXAMPLES 1–5

Three mixtures were made up having the following composition.

| Part A | Part B | Part C |
|---|---|---|
| 600 g deionized water | 437.5 g ethyl acrylate | 175 g deionized water |
| 0.75 g Triton GR-5* | 77.2 g methacrylic acid | 2.0 g sodium bisulfite |
| 1.75 g sodium persulfate | | |

*dioctylsodium sulfosuccinate

Part A was charged to a 2 liter reactor and brought to 40° C. while under vigorous nitrogen purge. Eighteen milliliters of Part B was added to the reactor followed by all of Part C. The remainder of Part B was added over the next 2.5 hours while the temperature was held at 39–41° C. The latex was then digested at 60° C. for 1.5 hours, cooled to 30° C. and bottled. The latex contained 40.6% non-volatiles.

1125 g. of the above latex was added in a small stream over a period of 25 minutes to a slowly stirred solution of 187.16 g. 50% NaOH in 547.9 g. deionized water. After the polymer had all dissolved, the viscous solution was heated at 50° C. for 22 hours to complete the saponification. The resulting solution (25.4% solids) had a Brookfield viscosity of 16,200 cps at 25° C. (No. 5 spindle, 10 rpm). The polymer is 50% ethylacrylate by moles with the remainder being sodium acrylate and methacrylate.

Samples of the above solutions were blended with Kymene 557 ® (a liquid adduct of epichlorohydrin and a polyamide having about 12.5% solids, a pH from 4.6–4.9, and a nitrogen content of about 12.8%) and cast on polished chromium plate with a 25 mil draw bar. After air drying, the flms were lifted from the plate and placed in a 95° C. oven for various times. The absorbency (gel capacity) of the various films in a 0.27 N NaCl solution is set forth in Table I.

TABLE I

| Example | Wt. % Curing Agent* Based on dry Wt. of Polymer | Time in Oven | Absorbency (gms solution/ gms film) |
|---|---|---|---|
| 1 | 0.847 | 10 min. | 38 |
| 2 | 0.847 | 25 min. | 37 |
| 3 | 0.6 | 10 min. | 51 |
| 4 | 0.6 | 25 min. | 50 |

TABLE I-continued

| Example | Wt. % Curing Agent* Based on dry Wt. of Polymer | Time in Oven | Absorbency (gms solution/ gms film) |
|---|---|---|---|
| 5 | 0.5 | 10 min. | 54 |

*Kymene 557 (Hercules, Inc.)

EXAMPLE 6

Following the procedures of the above examples, a film of the above polymer solution containing 0.5% of Kymene 557 was cast on an aluminum plate heated to 150° C. and then the plate was placed in a 150° C. oven for two minutes. The crosslinked polymer was scraped off the plate with a razor blade and the absorbency was 50 gms solution per gram polymer.

EXAMPLES 7-9

Films prepared in the manner of Examples 1-5 were allowed to cure at 25° C. for 48 hours in the laboratory. The atmosphere absorbency was then determined with allowance made for moisture absorbed from the air. The results are set forth in Table II using the NaCl solution of Examples 1-5.

TABLE II

| Example | Wt. % Curing Agent | Absorbency (gms solution/gms film or g/g) |
|---|---|---|
| 7 | 0.847 | 46 |
| 8 | 0.6 | 54 |
| 9 | 0.5 | 50 |

Comparative Experiments

In order to illustrate the improvements in curing rates over the above mentioned U.S. Pat. No. 3,980,663, the following experiment was performed.

A diglycidyl ether cross-linking agent (DER 736) was used at a recommended level of 0.3% by weight of the polyelectrolyte. The oven was adjusted to 110° C. It is known that many chemical reaction rates double for every 10° increase in temperature. A film was prepared as in the above examples and placed in the 110° C. oven for 5 minutes to 30 minutes. Even after 20 minutes, no gel was obtained after exposing the film to 0.27 N NaCl solution. After 30 minutes a very slimey, under crosslinked gel of 89 g/g absorbency was obtained. Allowing the same film to cure at room temperature for 2 days produced only a somewhat thickened solution when the film was placed in the salt water. That the level of diglycidyl ether was sufficient to cause cross-linking is evidenced by the fact that leaving the film at 110° C. for 16 hours did produce an absorbent film with an absorbency of 45 g/g.

EXAMPLES 10-12

A sample of polyacrylic acid (Acrysol A-5 from Rohm & Haas) was brought to pH 9.2 with sodium hydroxide to give a solution of polysodium acrylate of 24.6% solids content. This was then diluted with water to a 12.3% solids content, mixed with various amounts of Kymene 557, and the mixture was used to cast a 15 mil film on glass plates. These were then dried in an air circulating oven at 105° C. for thirty minutes. The absorbency results are shown in Table III.

TABLE III

| Example | level of Kymene (% based on solids content of polysodium acrylate | Absorbency (in g/g using 0.27 N NaCl |
|---|---|---|
| Control 1 (Ex. 25 of USP 3,224,986) | 20 | 11.2 |
| 10 | 5 | 25 |
| 11 | 4 | 31 |
| 12 | 3 | 34 |
| Control 2 | 0.5 | soluble |

These data show that for this particular polyelectrolyte, amounts of Kymene 557 at 0.5% or less do not give a crosslinked gel but a solution. On the other hand, amounts of the crosslinker greater than about 5%, give a gel which is too crosslinked to be useful, i.e., the absorbency is not sufficient to be of a practical value.

EXAMPLE 13

The crosslinkable solution prepared in Example 1 is coated on a laboratory paper towel, a polystyrene meat tray, a thin polyurethane foam sheet and cured at room temperature. Increased absorption is observed due to the water absorbent polymer coated thereon.

EXAMPLE 14

The polyelectrolyte prepared in Example 1 is mixed with 2.0 grams of Kymene 557 and the mixed solution diluted with water to a solution having 22% total solids with 0.5% of the solids being Kymene 557.

The solution is then cast on two glass plates coated with Panshield ® (for quick release) with a spreader to achieve 15 mil films. One plate was air dried for 48 hours in the laboratory air at 25° C. and at 40–50% relative humidity. The other plate was heated in an air circulating oven for 10 minutes at 107° C. The first plate had an absorbency of 54 gms of saline solution per gram of resin and the second had an absorbency of 56 gms of saline solution per gram of resin.

This shows that a relative short curing period at 107° C. can achieve the same results as a long period of curing at 25° C.

I claim:
1. A low temperature curing composition useful to form water absorbent articles of a carboxylic synthetic polyelectrolyte which comprises a solution of
   (1) a member selected from the group consisting of water, lower alcohols, and mixtures thereof,
   (2) about 5 to about 60% by weight based on the amount of (1) of a carboxylic polyelectrolyte or mixture thereof, and
   (3) about 0.5 to about 5.0 percent based on the weight of the polyelectrolyte of a water soluble polyamido-polyamine/epichlorohydrin adduct which is sufficient to cure said polyelectrolyte into a useful water absorbent article.
2. The composition of claim 1 wherein the amount of carboxylic polyelectrolyte is about 15 to about 40% by weight.
3. The composition of claim 1 wherein the carboxylic polyelectrolyte is an ammonium or alkali metal salt of the homopolymers of acrylic acid or methacrylic acid.
4. The composition of claim 3 wherein the amount of homopolymer is about 15 to about 40% by weight.
5. The composition of claim 1 wherein the carboxylic polyelectrolyte is an ammonium or alkali metal salt of the copolymers of acrylic or methacrylic acid with monoethylenically unsaturated monomers.
6. The composition of claim 5 wherein the amount of copolymer is about 15 to about 40% by weight.
7. The composition of claim 5 wherein the carboxylic polyelectrolyte consists of a terpolymer of ethyl acrylate, sodium acrylate, and sodium methacrylate with 50 mole percent being ethyl acrylate.
8. The composition of claim 3 wherein the carboxylic polyelectrolyte consists of polysodium acrylate.

* * * * *

UNITED STATES PATENT AND TRADEMARK OFFICE
CERTIFICATE OF CORRECTION

PATENT NO. : 4,132,695

DATED : January 2, 1979

INVENTOR(S) : N. D. Burkholder

It is certified that error appears in the above–identified patent and that said Letters Patent are hereby corrected as shown below:

Col. 1, line 17; change "the" to --that--.

Col. 2, line 2; change "of" to --or--.

Col. 3, line 56; change "precent" to --percent--.

Col. 4, line 19; after '20' insert --and--.

Col. 4, line 57; change "flms" to --films--.

Col. 6, line 44; change "mixture" to --mixtures--.

Signed and Sealed this

Nineteenth Day of June 1979

[SEAL]

Attest:

RUTH C. MASON
Attesting Officer

DONALD W. BANNER
Commissioner of Patents and Trademarks